United States Patent [19]

Shetty et al.

[11] Patent Number: 5,256,557
[45] Date of Patent: Oct. 26, 1993

[54] PURIFIED ALKALINE PROTEASE CONCENTRATE AND METHOD OF PREPARATION

[75] Inventors: Jayarama K. Shetty, Elkhart; Chimanbhai P. Patel, Mishawaka, both of Ind.; Mary A. Nicholson, Portazi, Mich.

[73] Assignee: Solvay Enzymes, Inc., Houston, Tex.

[21] Appl. No.: 813,705

[22] Filed: Dec. 27, 1991

[51] Int. Cl.$^5$ .......................... C12N 9/56; C12N 9/54
[52] U.S. Cl. ...................................... 435/222; 435/221
[58] Field of Search ................................ 935/222, 221

[56] References Cited

U.S. PATENT DOCUMENTS

| | | | |
|---|---|---|---|
| 3,623,957 | 11/1971 | Feldman | 435/222 |
| 4,689,297 | 8/1987 | Good et al. | 435/174 |
| 5,041,377 | 8/1991 | Becker et al. | 435/220 |

FOREIGN PATENT DOCUMENTS

WO89/05863 6/1989 PCT Int'l Appl. .
WO91/09943 7/1991 PCT Int'l Appl. .

OTHER PUBLICATIONS

Horvat, T. et al. (1987), *Eur. Congr. Biotechnol.* (2), pp. 605–608.
Henry S. D., *Cross Flow Filtration Recent Dvpts.*, Sep. Science (1972).
Bauer et al., *J. Chem.*, 5(3), pp. 117–120 (1967).
N. C. Beaton, Appl. of Ultrafiltration to Ferment. Prod., *Polymer Science Technology*, 13 (1980).
Bradford, *Anal. Biochem.*, vol. 72, pp. 248–254 (1976).
Fields, R., *Methods In Enzymology*, vol. 25, pp. 464–466 (1972).
Priest, F. G., Goodfellow, M. & Todd, C., *A Numerical Classication of the Genus Bacillus*, Journal of General Microbiology, vol. 134, pp. 1847–1882 (1988).
C. Starace and M. C. Barford, *Encyclopedia Chem. Technol.*, 9, 138–148 (1980).
K. Horikoshi, T. Akika, *A New Microbial World*, Springer-Verlag, N.Y. p. 93 (1982).
M. Dixon, E. D. Webb, *Enzymes*, Academic Press, N.Y., pp. 37–41 (1964).
Curline, *Methods of Plasma Protein Fractionation*, Academic Press, N.Y. (1980).

Primary Examiner—Douglas W. Robinson
Assistant Examiner—Jeffrey J. Sevigny
Attorney, Agent, or Firm—Willian Brinks Olds Hofer Gilson & Lione

[57] ABSTRACT

A highly purified alkaline protease preparation is produced by separating a mixture containing amorphous form and crystalline form of alkaline protease from ultrafiltrate containing impurities, through a method which includes the incubation of an aqueous alkaline protease concentrate with sodium chloride and carbohydrate hydrolyse enzymes at an elevated temperature greater than 20° C. and a pH between pH 4.0 and pH 6.5 at constant agitation.

8 Claims, 4 Drawing Sheets

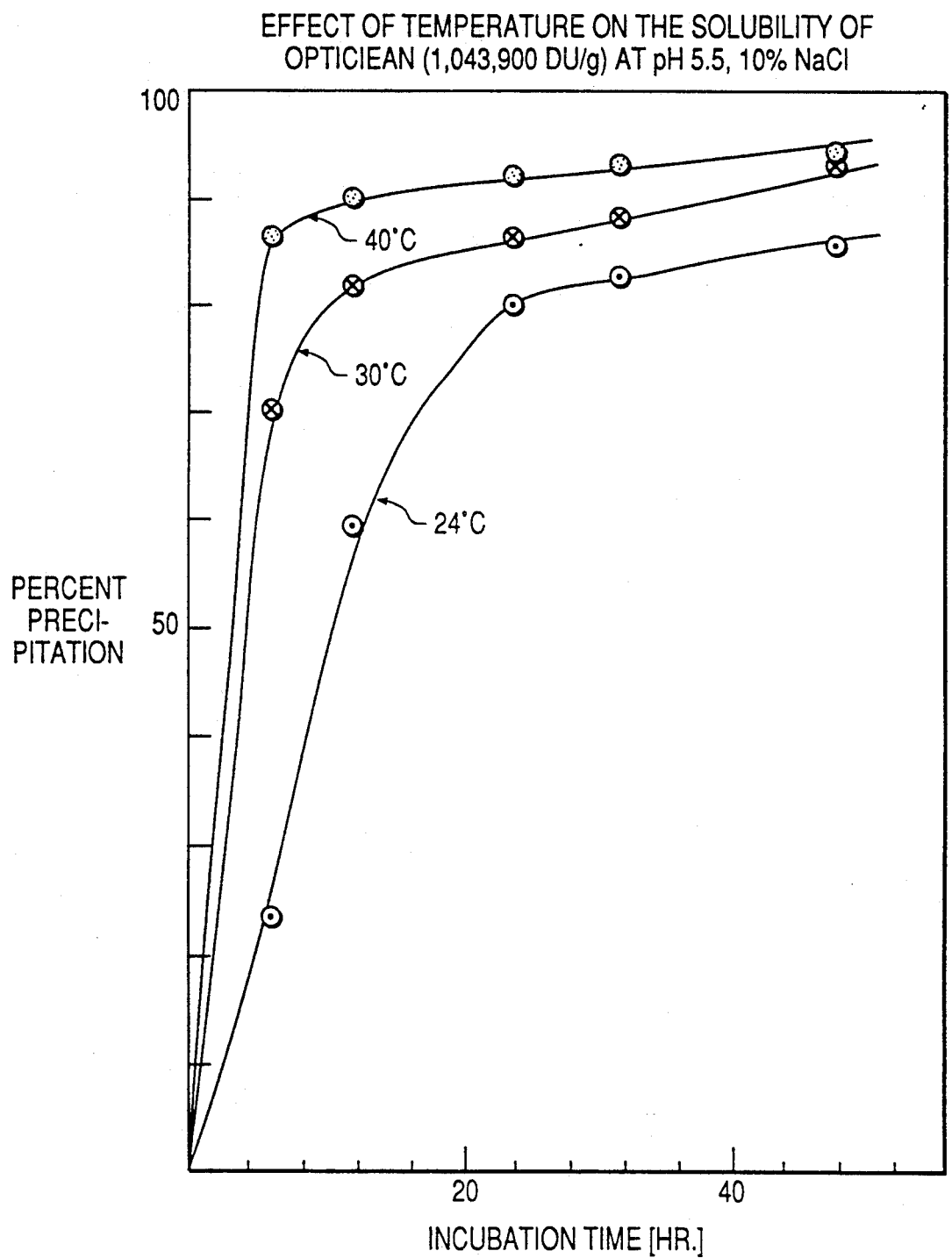

UF CONC = ACID HYDROLYSIS, 4HR.

UNPURIFIED

| RETENTION TIME OF THE PEAKS | SUGAR |
|---|---|
| 8.09 MIN. | GLUCOSE |
| 8.64 MIN. | GALACTOSE |
| 15.36 MIN. | PROPYLENE GLYCOL |

PURIFIED (SODIUM CHLORIDE PRECIPITATION)

HIGHLY PURIFIED (SODIUM CHLORIDE & ENZYME TREATMENT)

PURIFIED ALKALINE PROTEASE CONCENTRATE AND METHOD OF PREPARATION

BACKGROUND OF THE INVENTION

The present invention relates to enzyme recovery and purification and, more particularly, to a process for the recovery of a purified alkaline protease from *Bacillus licheniformis* and *Bacillus alcalophilus*, or genetically engineered variants of these, and the composition that results from that process.

The use of enzymes in detergents is well known. Generally, enzymes used for detergent purposes have primarily been the alkaline stable proteases, lipases and alpha-amylases. Of the alkaline proteases, serine proteases derived from Bacillus species, namely *Bacillus subtilis*, *Bacillus licheniformis*, and alkalophilic Bacillus bacteria have been widely used in detergent formulations. (Starace C. and Barford, H. C., *Encyclopedia Chem. Technol.* 9, pp. 138-148 (1980); Koki Horikoshi and Terahiko Akika, *A New Microbial World*, Springer-Verlag, N.Y., p. 93 (1982)).

Enzymes constitute only a small portion of most liquid detergent formulations. Thus, it is necessary to produce fairly concentrated enzyme preparations. Enzyme concentrates are traditionally prepared by removing the water from aqueous solutions of the enzymes using conventional methods such as ultrafiltration and evaporation.

Inorganic salts such as ammonium sulphate and sodium sulphate have been used extensively to precipitate enzymes from aqueous solution at laboratory and commercial levels. (Dixon, M. and Webb, E. D., *Enzymes*, Academic Press, N.Y., pp. 39-41 (1964), Curline, *Methods of Plasma Protein Fractionation*, Academic Press, N.Y. (1980)). The widespread use of these salts on a large scale, however, can pose environmental problems and complicate waste water treatment, in fact, many countries in Europe have already restricted large scale industrial use of these salts. Organic solvents such as ethanol and acetone are also used as precipitants (Dixon and Webb, *Enzymes, supra*, pp. 37-39; Bauer et al,. *J. Chem.*, 5(3), pp. 117-20 (1967)), however, their use has been limited because of cost and concern for safety.

Environmentally safe and cost effective enzyme purification methods are discussed in, for example, Becker et al., U.S. Pat. No. 5,041,377, describing a method of producing crystalline subtilisin derived from *Bacillus subtilis* and *Bacillus amyloliquifaciens* by the addition of a halide salt to an alkaline protease solution at temperatures less than 10° C. and at a pH range from 5.2 to 5.8..

The color and odor of protease can adversely effect the quality of the detergent formulations in which they are incorporated. This necessitates the removal of pigments from the enzyme concentrate, which pigments are believed to be a part of an enzyme-pigment complex. Dixon, M. and Webb, E. C., *Enzymes, supra*, reported solvent precipitation methods to remove pigment from protease solution. This method, however, resulted in poor product yield. Absorption of pigments with activated carbon from aqueous enzyme concentrate is generally practiced in industrial applications, however, material loss, high cost and waste disposal present major drawbacks.

It is desirable that alkaline protease preparations for detergent applications be free from components which can cause undesirable color, haze, instability and allergic activity in the final product. These components may be derived from the microorganism themselves or from residual fermentation raw materials. In preparations of gram positive Bacilli, cell wall anionic polymers, peptidoglycans and other polysaccharide contaminants become solubilized during cell growth due to cell wall turnover. The presence of these bacterial cell wall polymers in alkaline proteas preparations can cause several undesirable effects including an increase in the allergenicity, a decrease in enzyme stability by binding cations, e.g., $Ca^{++}$, and may cause haze formation in detergent formulations. Patent Cooperation Treaty ("PCT") Patent Application No. WO89/05863 published Jun. 29, 1989 discloses a method to separate these polymers from protease preparations using ion-exchange chromatography. This method is difficult for a large scale operation and expensive. There is a need for a simple and cost-effective method of removing carbohydrate contaminants in general, and galactosyl polymers in particular, from alkaline protease preparations.

Another problem that exists in preparing purified alkaline protease product is a loss of enzymatic activity due to autolytic degradation during either processing or storage. Alkaline proteases perform the function of hydrolyzing protein molecules in the bacterial environment. Their catalytic activity is based on cleavage of the peptide bond in protein molecules and a resultant breakdown of the protein structure into small polypeptides and individual amino acids. Because the alkaline protease is itself a protein molecule, alkaline proteases will begin to hydrolyze other alkaline protease molecules in solution under the proper conditions. While this is a general problem with protease preparations, loss of proteolytic activity as a result of autolytic degradation of alkaline protease may adversely effect the performance of the enzyme under extreme conditions present in detergent formulations, e.g., alkaline pH, because the alkaline protease is most catalytically active at the alkaline pH ranges.

None of the patents, patent applications or publications described above provide the important advantages of an alkaline protease preparation free of haze and odor forming contaminants, allergy causing activity and other undesired fermentation derived impurities. Thus, a need exists for a simple and efficient process for purifying alkaline protease while limiting autolytic degradation of the protease during the purification procedure. The ability to effectively remove allergenic properties and other undesirable characteristics from alkaline protease preparations is critical for effective and safe commercial protease utilization.

SUMMARY OF THE INVENTION

It is an object of this invention to provide for a method of purifying alkaline protease which removes pigments associated with haze, color contamination and odor in commercial alkaline protease preparations.

It is a further object of this invention to provide for a simple and novel method for the purification of alkaline protease which removes polysaccharides and oligosaccharides which are responsible for problems associated with allergenic activity.

It is a further object of this invention to provide a method of purification of alkaline protease with significantly reduced autolytic degradation.

It is a further object of this invention to achieve the above mentioned objects without the use of environmentally dangerous or costly chemicals.

It is a further object of this invention to provide a method for the purification and recovery of an alkaline protease product which is more efficient and results in a substantially improved yield, e.g., over 90%, when compared to those procedures recognized in the prior art.

According to the invention, a method is provided for the preparation of purified alkaline protease from a fermentation broth, the alkaline protease being derived from either *Bacillus licheniformis* or *Bacillus alcalophilus*, or a genetically engineered mutant thereof. The method comprises forming an alkaline protease solution by separating alkaline protease from cells and suspended solids in the fermentation broth, adding to the alkaline protease solution hydrolytic enzymes and sodium chloride, incubating the mixture to separate the alkaline protease from hydrolyzed polymeric impurities and dissociate the alkaline protease from pigments, and collecting the resulting purified alkaline protease precipitate.

Preferably, this embodiment is conducted with the addition of the hydrolytic enzymes and sodium chloride to the alkaline protease solution occurring at about the same time. Optionally, the addition of hydrolytic enzymes may precede the addition of sodium chloride.

Preferably, the alkaline protease solution is concentrated prior to the addition of sodium chloride. More preferably, this embodiment is carried out under conditions of agitation, preferably constant and vigorous agitation, during the addition of sodium chloride. Even more preferably, for alkaline protease derived from *Bacillus alcalophilus*, the solution conditions upon the addition of sodium chloride are defined by a pH between about 4.0 and 7.5, a temperature between about 28° C. and 32° C., and a sodium chloride concentration of about 8.0–12.5% w/v. For *Bacillus licheniformis*, the pH range of the solution is between about 4.5 and 9.5, with the temperature and sodium chloride concentration being about the same as above.

The compositions made according to this invention are characterized by and have the advantages of a high level of purity, e.g., less than 0.65 mg galactosyl polymer per gram of enzyme and a pigment content defined by absorbance of less than 1.3 at 470 nm. These compositions are also characterized by a substantial decrease in odor, color contamination and allergenicity, and an increase in stability.

The invention, together with further objects and attendant advantages, will best be understood by reference to the following description, drawings, examples, and tables herein. However, the invention is not limited thereto.

BRIEF DESCRIPTION OF THE DRAWINGS

FIG. 3 is a graphical depiction of the effect of temperature on the solubility of alkaline protease derived from *Bacillus alcalophilus* at pH 5.5, 10% sodium chloride weight/volume.

DETAILED DESCRIPTION OF THE INVENTION

Figure 1A:
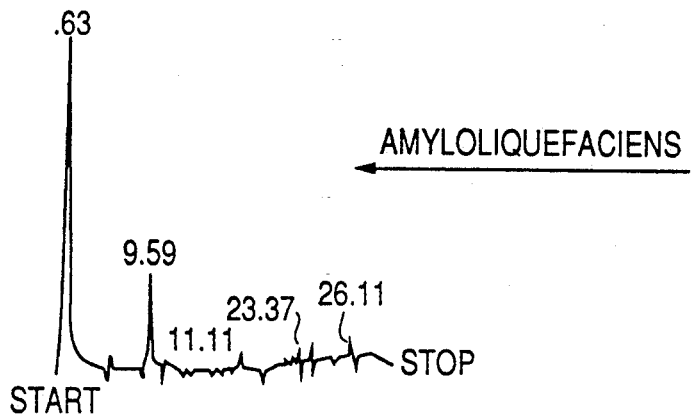
FIG. 1 illustrates the high performance liquid chromatography patterns of purified alkaline protease derived from *Bacillus amyloliquefaciens, Bacillus licheniformis* and two strains of *Bacillus alcalophilus*.
Figure 1B:
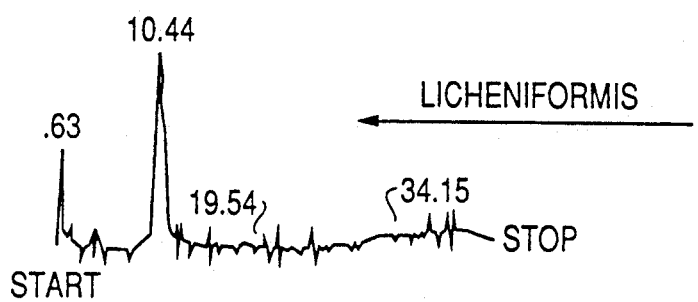
Figure 1C:
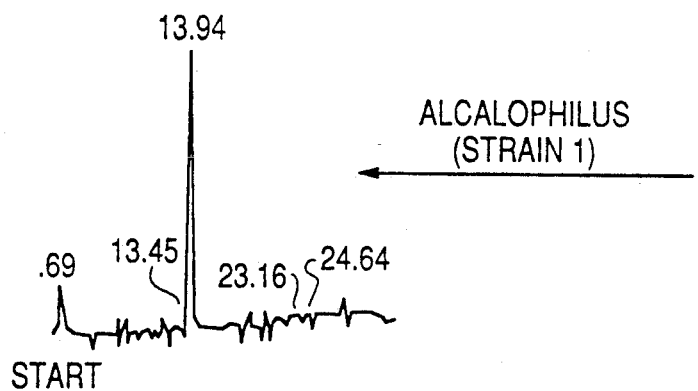
Figure 1D:
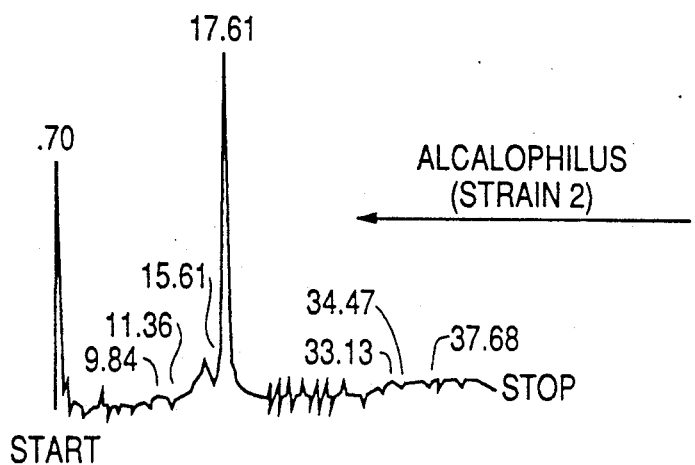

In accordance with a preferred embodiment of the present invention, a purified alkaline protease solution with reduced polysaccharide and galactose polymer content is prepared. The present invention specifically contemplates fermentation mixtures of either *Bacillus licheniformis* or *Bacillus alcalophilus*. A suitable source of *Bacillus alcalophilus* alkaline protease is the product sold under the tradename Opticlean ®, and a suitable source of *Bacillus licheniformis* alkaline protease is the product sold under the tradename Optimase ®, both of which are available from Solvay Enzymes, Inc., of Elkhart, Ind.

For cultivation of *Bacillus alcalophilus* and *Bacillus licheniformis* strains usually a solid or liquid culture medium is used which contains an alkaline buffer as well as components necessary for the microorganisms' growth, i.e., a carbon source, a nitrogen source and inorganic salts. The buffer should maintain the medium's pH at a level between 7.0 and 10.0. Suitable carbon sources include mannose, fructose, mannitol, maltose, cellobiose, sucrose, dextrin, starch, molasses, glucose, hydrolysed starch or a blend of two or more of these carbon sources. Nitrogen sources which can be used include soybean flour, casein, corn steep liquor, cotton seed meal, enzymatic hydrolyzates of available proteins, dried yeast, yeast extract, fish meal, potato meal or a blend of two or more of these nitrogen sources. Potassium phosphate and magnesium sulfate represent suitable salts. Examples of suitable alkaline buffers include sodium carbonate, potassium carbonate, sodium bicarbonate, sodium phosphate and sodium tetraborate. Alternatively, an automatic pH control scheme may be employed by the addition of various other organic or inorganic substances necessary for the growth of the bacterial strains and the production of enzymes. The medium containing the above components is sterilized in a conventional manner and inoculated with one of the strains of the present invention. Cultivation may be conducted aerobically with shaking or under aerated agitation preferably at 30° C. to 40° C. for 30 to 120 hours to obtain a culture fluid.

After fermentation, the microbial cells and various suspended solids, including residual raw fermentation materials, are removed by conventional separation techniques. The alkaline protease solution is concentrated into a concentrated alkaline protease solution using ultrafiltration until the desired protease activity is obtained. A suitable concentration is 400 DAPU/gm for *Bacillus licheniformis* alkaline protease, and 1,000,000 Delft units/g for *Bacillus alcalophilus* alkaline protease.

The ultrafiltration concentrate solution is combined with hydrolytic enzymes, such as pectinase and glucoamylase, which enzymes act to hydrolyze polysaccharide impurities. Hydrolytic enzymes are enzymes which hydrolyse polysaccharides including oligosaccharides, amylases, alpha amylases, pullulanases, transferases, polysaccharide hydrolases, glycosylhydrolases, galactosyl hydrolases, pectinases and gluconases. Examples of suitable hydrolases are Clarex ® pectinase and Diazyme ® L-200 glucoamylase, available from Solvay Enzymes, Inc., Elkhart, Ind.

Simultaneously with the hydrolytic enzymes, sodium chloride is added to a concentration of 10.0% weight/volume. The solution is adjusted to a pH of between about 4.5 and 6.5 and maintained at a temperature between about 28° C. and 32° C. for a suitable period of time. Generally, between about 48 and 72 hours will be sufficient to allow hydrolysis of the various polysaccharide and oligosaccharide contaminants.

The purified alkaline protease containing a heterogeneous mixture comprising amorphous precipitant with irregular structures, and/or varying degrees of ordered structures, was then separated from the dissociated pigment and other galactosyl impurities and collected by filtration. Cross membrane microfiltration has been utilized for this purpose with excellent results. The degree of ordered structures or crystals depends upon the conditions applied.

It is preferred to vigorously agitate the mixture subsequent to the addition of hydrolytic enzymes and sodium chloride and to continue the agitation through collection of the precipitate.

Various alternative embodiments are possible. For example, in a preferred embodiment solid sodium chloride is added when using alkaline protease derived from *Bacillus alcalophilus*, the sodium chloride concentration should be between 8.0% to 12.5% w/v and most preferably 10.0% w/v. The temperature should generally be above about 20° C., usually above about 25° C. and preferably between about 28° C. and 32° C. When working with alkaline protease derived from *Bacillus licheniformis*, the sodium chloride concentration should generally be between about 2.5% and about 20.0% w/v, usually between about 7.5% and about 15.0% w/v, and preferably between about 10.0% and 12.5% w/v.

The pH of the mixture during hydrolysis should generally be kept below 6, and preferably below 5.5. Precipitation, if performed as a separate step from hydrolysis, should generally be maintained at between a pH of about 4.0 and 7.5 for alkaline protease derived from *Bacillus alcalophilus*, while for *Bacillus licheniformis* the pH should generally be maintained between 4.5 and 9.5. In a preferred embodiment, the pH is kept between 4.5 and 6.5 during both the hydrolysis and precipitation procedures.

Suitable hydrolytic enzymes include enzymes which hydrolyze starch and pectins, including the pectinases, glucoamylases, and alpha amylases. These enzymes are commercially available. In general, these enzymes do not function efficiently in the alkaline pH ranges, and it is necessary to maintain a relatively acidic pH during hydrolysis. The polymeric impurities that are undesirable include cell wall anionic polymers, peptidoglycans, and galactose polymer and other poly- and oligosaccharide contaminants that become solubilized during fermentation of Bacilli organisms.

Enzymatic hydrolysis and the addition of sodium chloride may be carried out sequentially or simultaneously. If the sodium chloride is added subsequent to hydrolysis, the solution may be maintained at a constant pH and temperature throughout the hydrolysis and precipitation. Generally, the 48 to 72 hour period required for hydrolysis will suffice to also allow complete dissociation of the enzyme-pigment complex and salting-out of the purified alkaline protease; however, in the embodiment including sequential hydrolysis-precipitation functions, the precipitation should be allowed to precipitate for 48 to 72 hours to allow completion of the precipitation reaction. Although it is believed that the pigment-enzyme complex is dissociated immediately upon the addition of sodium chloride, the precipitation reaction takes between 48 and 72 hours to complete. This embodiment allows flexibility in selecting wide pH ranges for the different steps in the purification process. For example, it may be desirable to maintain the pH during enzymatic hydrolysis in the acidic range (e.g., for alkaline protease derived from *Bacillus alcalophilus*, pH values as low as 4.0 can be maintained, and with alkaline protease from *Bacillus licheniformis*, the pH may be maintained as low as about 4.5 without inactivation) while the precipitation step may be carried out at a higher pH to take advantage of the higher precipitation percentages. (See Example 5.)

Nonetheless, it is believed that it is simpler and equally as effective to carry out hydrolysis and the addition of sodium chloride simultaneously at a low pH. As indicated, the autolytic activity of an alkaline protease is minimal at low pH levels, e.g., from 4.0 to 6.5, and it is believed that any loss in precipitation percentage at low pH is likely made up for by a decrease in autolytic degradation due to decreased autolytic activity of alkaline proteases in the acidic ranges.

The purified alkaline protease made according to this method will generally have a substantially reduced level of impurities; e.g., absorbance of less than 1.3 at 470 nm; a galactosyl polymer content of less than 1.0 mg/g of enzyme, and preferably less than 0.65 mg/g of enzyme; and being essentially amorphous and presenting a crystalline structure content of less than 40%, and preferably less than 20%, as measured by standard techniques such as x-ray crystallography.

Alternative embodiments are contemplated without departing from the spirit of the present invention. Fermentation, separation, and concentration are well known in the art and conventional methods can be used to achieve the desired results. Conventional separation techniques can be utilized to separate the alkaline protease from microbial cell components and suspended solids that occur during the fermentation process. Filtration, centrifugation, microfiltration, rotary vacuum filtration or the like will generally suffice. Concentration of the alkaline protease solution may be achieved by any of a variety of conventional techniques including ultrafiltration, evaporation, extraction, chromatography or precipitation followed by redissolution. It is desirable to concentrate the protease solution in order to optimize yield upon precipitation. Use of unconcentrated solutions will require an increased precipitation time to collect the purified alkaline protease. Collection of the alkaline protease can be effected by any method known in the art, including centrifugation, vacuum drum filtration, press filtration or cross flow membrane microfiltration. The resulting "purified" enzyme is essentially free from galactosyl polymers.

In a variation of this invention, a method of preparing a purified alkaline protease solution is defined. One preferred embodiment of the present invention involves a purified alkaline protease produced through the following method. *Bacillus licheniformis* or *Bacillus alcalophilus* is cultivated in a suitable fermentation medium. After fermentation, the microbial cells and various suspended solids including residual fermentation raw materials are removed. The remaining alkaline protease solution is further concentrated into a concentrated alkaline protease solution using ultrafiltration until the desired protease activity is obtained.

The concentrated alkaline protease solution is adjusted to a pH of about 5.0 and a temperature of about 30° C. and sodium chloride is added to a final concentration of about 10.5% weight/volume. The resulting incubation mixture is allowed to incubate for a period of between about 48 and 72 hours in order to allow completion of the precipitation reaction. The purified alkaline protease precipitate is then separated from the supernatant and collected by cross flow membrane microfiltration.

Alkaline proteases exhibit maximum activity in the alkaline pH region, i.e., about pH 8.5–11.0. As indicated, in FIG. 2 and Example 10, it is apparent that autolytic degradation increased at higher pH, resulting in decreased yield. It is necessary, in order to obtain optimal efficiency of an enzyme purification recovery system, that any system of controlling proteolytic, and thus autolytic, activity be reversible.

The precipitation of various Bacillus alkaline protease will vary with respect to the isoelectric pH of the specific protein in question, surface hydrophobicity, and any impurities (polymeric) that are present in the medium. Applicants believe that the difference between these Bacillus derived alkaline protease molecules is marked. For example, according to Priest et al., infra, there is now evidence that the genus Bacillus encompasses some 80 taxa of approximate species rank that can be assigned to five or more cluster-groups. These should be used as a framework for redefining the current genus and splitting it into several genera. For example, Cluster-group B2 contains cluster 14 (*Bacillus amyloliquefaciens*), cluster 15 (*Bacillus subtilis*), cluster 20 (*Bacillus licheniformis*) and cluster 24 (*Bacillus firmus*). Cluster-group C contains cluster 25 (*Bacillus firmus*) while Cluster-group E contains cluster 44 (*Bacillus lentus*). *Bacillus firmus* and *Bacillus lentus* are alkalophilic species. Priest, F. G., Goodfellow, M. and Todd, C., *A Numerical Classification of the Genus Bacillus*, Journal of General Microbiology 134, pp. 1847–1882 (1988).

The difference in properties of the various alkaline proteases is also well illustrated in alkalophilic microorganisms, Horikoshi et al., Table 6.1, page 25 (1982). Further, as shown in FIG. 1, the HPLC patterns of purified enzymes from different Bacillus species illustrate the dramatic differences between the species, i.e., amyloliquefaciens, *Bacillus licheniformis* and two different strains of *Bacillus alcalophilus*.

Concentrated alkaline protease solids or solutions prepared according to one of the embodiments of the present invention are useful for all applications to which alkaline proteases are utilized in either solid or liquid form. These preparations can be made into a final product that is either liquid solution, solid, granular, powder or a slurry. In particular, they can be used in laundry detergents and spot removers, as contact lens enzymatic cleansing systems, as a depilatory in tanning, in the food industry for the preparation of protein hydrolysates and in blood serum testing procedures for the detection of incomplete antibodies.

It is particularly advantageous for use in detergents and cleansers because the alkaline proteases prepared according to this invention have a lessened pigment content and thus have a reduced level of haze formation, odor and color contamination. Moreover, the removal of allergenic properties of galactosyl polymers in alkaline protease preparations prepared according to the embodiments of this invention are especially useful in contact lens products, and other commercial applications, for food, feed and detergent industry.

The following examples, related tables, and drawings are intended to further illustrate the invention. It will be understood, however, that the invention is not limited to these specific examples or the embodiments expressed therein.

EXAMPLE 1

The Effect of Different Concentrations of Sodium Chloride

Alkaline protease was produced from a fermentation broth of a submerged culture of *Bacillus licheniformis* in a suitable medium. After the fermentation, the microbial cells and suspended solids were separated from the alkaline protease by conventional means such as centrifugation and/or vacuum drum filtration. The resultant alkaline protease solution was then concentrated using ultrafiltration. Different amounts of sodium chloride were added to 40 ml aliquots of the ultrafiltration concentrated alkaline protease solution and the activity adjusted to 550 detergent alkaline protein units/ml (DAPU/ml). The pH was adjusted to 5.5 using 10% acetic acid, and the treated samples diluted to 50 ml with distilled water and incubated at 37° C. for 3 hours. A control sample was kept at 5° C. After the specified time, solutions were centrifuged to separate the precipitated enzyme from the supernatant. The clear filtrates were analyzed for total protein and enzymatic activity. (Table 1).

The level of total protein in the purified alkaline protease precipitate, and thus the percentage of total proteins precipitated, was determined utilizing a protein-dye binding method (Bradford, *Anal. Biochem*, 72, 248 (1976). An aliquot of protein solution (0.1 ml) was pipetted into a test tube and 5 ml of the protein-dye (Bio-Rad) reagent added thereto followed by vortex mixing of the contents. The absorbance at 595 nm was measured after 5 minutes against a reagent blank prepared from 0.1 ml of water and 5 ml of protein-dye reagent. The amount of protein was then determined from a standard curve prepared by bovine gamma globulin.

The percentage of alkaline protease present in the purified *Bacillus licheniformis* alkaline protease product was determined through an assay based on hydrolysis of casein substrate at 40° C., at pH 8.5 (borate buffer). Unhydrolyzed casein was precipitated with trichloroacetic acid and removed by centrifugation. The absorbance of the trichloroacetate soluble casein-hydrolysate was measured in a spectrophotometer at 275 nm. One detergent alkaline protease unit (DAPU) is that activity which will liberate the equivalent of four micromoles of tyrosine per minute under the condition of the assay. The total alkaline protease activity value (DAPUs) of the supernatant solution was compared to the non-precipitated control to determine the percentage of the total pre-purification alkaline protease that was precipitated from solution. For alkaline protease derived from *Bacillus alcalophilus*, the assay is carried out in a borate buffer at pH 8.7. The enzymatic activity is based on the Delft unit which is defined as following. If 1 ml of a 2% solution of an enzyme preparation gives a difference in absorbance of 0.400 under the test conditions, then the enzyme preparation has a protease activity of 1000 Delft units.

TABLE 1

Effect of Sodium Chloride Concentration

| Sodium Chloride Concentration weight/volume | Proteins mg/ml | % precipitated | Enzyme Activity DAPU/ml | % precipitated |
|---|---|---|---|---|
| Control, 5° C., 3 hr | 66.0 | 0 | 559.5 | 0 |
| Control 37° C., 3 hr | 66.2 | 0 | 560.0 | 0 |
| 2.5% NaCl | 53.2 | 19.4 | 390.5 | 30.3 |
| 5.0% NaCl | 42.4 | 35.8 | 287.8 | 48.6 |
| 7.5% NaCl | 36.0 | 45.5 | 245.8 | 56.1 |
| 10.0% NaCl | 33.6 | 49.1 | 218.2 | 61.0 |
| 12.5% NaCl | 27.6 | 58.2 | 198.3 | 64.6 |
| 15.0% NaCl | 34.0 | 48.5 | 238.7 | 57.4 |
| 20.0% NaCl | 35.6 | 46.1 | 258.8 | 53.8 |

Incubation of alkaline protease at pH 5.5, 37° C. for 3 hours. had no effect on the stability of the enzyme. However, addition of sodium chloride caused the precipitation of the enzyme. The precipitation of the enzyme also increased with increasing concentration of sodium chloride and maximum precipitation of the enzyme occurred at 12.5% weight/volume sodium chloride level.

EXAMPLE 2

Effect of Temperature

The protease solution in this example was prepared substantially in accordance with Example 1, except that separate samples were incubated at varying temperatures. (Table 2).

TABLE 2

Effect of Temperature

| Trial | Protein mg/ml | % precipitated | Protease Activity DAPU/ml | % enzyme precipitated |
|---|---|---|---|---|
| Control. No. NaCl | 66.4 | 0 | 559.5 | 0 |
| 15% NaCl, 5° C. | 66.4 | 0 | 559.0 | 0 |
| 15% NaCl, 10° C. | 64.8 | 0 | 566.6 | 0 |
| 15% NaCl, 23° C. | 65.6 | 0 | 568.5 | 0 |
| 15% NaCl, 30° C. | 66.0 | 0 | 541.5 | 3.2 |
| 15% NaCl, 37° C. | 59.2 | 11 | 467.1 | 16.5 |
| 15% NaCl, 45° C. | 36.4 | 45.2 | 240.8 | 57.0 |

Temperature clearly has a strong impact on the degree of precipitation. At pH 5.5 and sodium chloride concentration of 15.0% weight/volume, no precipitation of alkaline protease occurred until the temperature reached 30° C. Substantial precipitation occurred above 37°.

EXAMPLE 3

Effect of Sodium Chloride at Low Temperature

The effect of sodium chloride on the separation of alkaline proteases was studied at temperatures of 5° C. and 10° C. for up to twelve days. To two 50 ml solutions of alkaline protease concentrate derived from *Bacillus licheniformis* 300 DAPU/g and 600 DAPU/g—and two 50 ml solutions of alkaline protease derived from *Bacillus alcalophilus*—500,000 Delft units/g and 1,000,000 Delft units/g)—solid sodium chloride was added to a final concentration of 10% weight/volume and the pH was adjusted to pH 5.5. The samples were then kept at 5° C. and 10° C. and examined for enzyme precipitation at daily intervals. No enzyme precipitate occurred at either temperature up to even 12 days. Sodium chloride is ineffective in causing the precipitation/separation of alkaline protease derived from *Bacillus licheniformis* or *Bacillus alcalophilus* from soluble impurities at low temperatures, whereas incubation temperatures greater than 20° C. cause separation/precipitation of the alkaline proteases in a matter of hours, as in Example 2.

EXAMPLE 4

Effect of Temperature on the Rate of Enzyme Separation

*Bacillus alcalophilus* alkaline protease (Opticlean ®) ultrafiltration concentrate (1,043,900 Delft units/g) containing 10% NaCl, pH 5.5 was incubated at 24° C., 30° C., or 40° C. (constant stirring). Samples (10 ml) were withdrawn at different intervals of time (6, 12, 24, 32 and 48 hrs) and centrifuged to separate the precipitated enzyme. The supernatant was then assayed for activity (FIG. 3).

EXAMPLE 5

Effect of pH

The activity of *Bacillus licheniformis* alkaline protease (Optimase ®) concentrate was studied by removing cells and suspended solids from a fermentation mixture and concentrating the resulting alkaline protease solution through ultrafiltration. The resulting alkaline protease concentrate was adjusted to an activity of 500 DAPU/ml. Sodium chloride was added to a concentration of 12.5% w/v and the pH was adjusted to 7.5, 7.0, 6.5, 6.0, 5.5 and 5.0 using 10% acetic acid (1+2 drops). The treated samples were incubated at 37° C. for three hours and centrifuged. The total protein and enzymatic activity were determined. (Table 3).

TABLE 3

Effect of pH on the Precipitation of *Bacillus licheniformis* Alkaline Protease

| pH | Proteins mg/ml | % precipitated | Enzyme Activity DAPU/ml | % enzyme precipitated |
|---|---|---|---|---|
| Control | 64.4 | 0 | 507.0 | 0 |
| pH 5.0 | 43.2 | 33.0 | 325.0 | 36.0 |
| pH 5.5 | 37.5 | 41.8 | 251.0 | 50.5 |
| pH 6.0 | 25.8 | 60.0 | 167.0 | 67.1 |
| pH 6.5 | 21.0 | 67.4 | 128.0 | 74.8 |
| pH 7.0 | 16.4 | 75.2 | 104.0 | 79.5 |
| pH 7.5 | 11.8 | 81.7 | 75.0 | 85.2 |

The effect of pH on the precipitation of alkaline protease in the presence of sodium chloride at 37° C. was marked. The percentage of enzyme precipitation increased with increasing pH to over 85% in three hours at pH 7.5 compared to 36% enzyme precipitation of pH 5.0.

EXAMPLE 6

Effect of Incubation Time

Four hundred ml aliquots of *Bacillus licheniformis* alkaline protease (Optimase ®) ultrafiltration concentrate of an activity of 600 DAPU/ml were transferred into two different beakers and 61.25 g of sodium chloride was added. The pH of the solutions were then adjusted to 6.0 and 7.5 separately, diluted to 500 ml and incubated at 37° C. The samples (50 ml) were withdrawn at different intervals of time. The precipitated protein was separated from the supernatant by centrifugation at 20,000 rpm for 20 minutes. The total protein and enzymatic activity were determined (Table 4).

TABLE 4

Effect of Incubation Time on Precipitation of
Bacillus licheniformis Alkaline Protease

| Sample pH Specification | Total Protein mg/ml | % precipitated | Enzyme Activity DAPU/ml | % enzyme precipitated |
|---|---|---|---|---|
| 6.0 0 time | 40.0 | 0 | 312.0 | 0 |
| 6.0 1 hr. | 36.0 | 9.0 | 232.9 | 25.4 |
| 6.0 2 hrs. | 26.0 | 34.0 | 168.2 | 46.1 |
| 6.0 4 hrs. | 18.6 | 53.0 | 120.3 | 61.4 |
| 6.0 6 hrs. | 14.4 | 64.0 | 93.2 | 70.1 |
| 7.5 0 time | 37.0 | 0 | 276.0 | 0 |
| 7.5 1 hr. | 11.2 | 70.0 | 71.2 | 74.2 |
| 7.5 2 hrs | 7.6 | 79.0 | 48.3 | 82.5 |
| 7.5 4 hrs. | 5.6 | 85.0 | 35.6 | 87.1 |
| 7.5 6 hrs. | 4.8 | 87.0 | 30.5 | 89.0 |

A large percentage of the alkaline protease was found in the precipitate after six hours. The extent and rate of precipitation of alkaline protease was dependent on the pH of the protein solution (Table 4). It is believed that the rate of precipitation becomes faster near the isoelectric point of the enzyme, which in the case of alkaline protease from Bacillus licheniformis is about 8.2 to 8.5.

EXAMPLE 7

Effect of Sodium Chloride on the Dissociation of Pigments From Alkaline Proteases To separate 100 ml aliquots of Bacillus licheniformis alkaline protease (Optimase ®) ultrafiltration concentrate, sodium chloride was added to a final concentration of 10% weight/volume. The pH of the sample was adjusted to 7.5 using 10% NaOH and incubated at 37° C. for four hours. The precipitated alkaline protease was separated by centrifuging at 20,000 rpm for 20 min. The precipitate was then solubilized in 50% propylene glycol (100 ml). The total proteins, enzyme activity and color ("pigments") at 470 nm were determined. For comparison, alkaline protease was precipitated with 65% (weight/volume) ammonium sulphate and 25% (weight/volume) sodium sulphate under identical conditions. (Table 5)

tinolytic enzyme Clarex ® (pectinase from Solvay Enzymes, Inc., Elkhart, Ind.) and glucoamylase Diazyme ® L-200 (glucoamylase from Solvay Enzymes, Inc., Elkhart, Ind.), caused the hydrolysis of galactosyl polymer and residual starch in protease concentrate at a pH 4.5-5.5 at 30°-40° C.

To 100 g of ultrafiltration concentrate of Opticlean ® (Bacillus alcalophilus alkaline protease), 2.5 g of the pectinase and 0.25 g of the glucoamylase were added. The solution was then adjusted to pH 5.2 and maintained at 30° C. Samples (5 g) were withdrawn at different intervals of time and the galactosyl polymer content was determined. The liberated galactose was then determined by HPLC analysis.

To 5 g of the Bacillus alcalophilus alkaline protease samples from the above example, 5 ml of 20% (weight/volume) trichloroacetic acid was added slowly while mixing to precipitate the protein. After standing in ice for 30 minutes, the mixture was centrifuged (15,000 rpm, 20 min. SS-34 rotor). The supernatant was decanted off into a clean tube and reagent grade alcohol (20 ml) added with mixing. After standing for 30 minutes at room temperature, the tube was centrifuged (10,000 rpm, 10 minutes), and the supernatant discarded. The pellet was redissolved in 0.1M acetate buffer, pH 4.0 (4.95 ml). To this was added Clarex ® pectinase 0.25 ml) and the mixture was incubated at 60° C. for two hours. After this time, 4N sulfuric acid (25 µl) was added to stop the reaction. The reaction mixture was filtered (0.45µ) and injected into a high performance liquid chromatography measurement device for quantification of free galactose as below. A substrate blank and an enzyme blank were also run. Total galactosyl polymer contained was determined by acid hydrolysis method.

The galactosyl polymer and residual starch may be determined by precipitating the protein with acid, incubating the supernatant at 100° C. for 24 hours to hydrolyze the polysaccharides and determining the galactose and glucose content of the hydrolyzate by high performance liquid chromatography. For example, to 5 ml of

TABLE 5

Comparison of Different Methods on the Precipitation of Alkaline
Protease and on the Removal of the Pigments

| Treatment | Protein mg/ml | % precipitated | Protease DAPU/ml | Activity % enzyme precipitated | Pigments OD at 470 nm | % removed |
|---|---|---|---|---|---|---|
| Control | 54 | 0 | 381 | 0 | 2.16 | 0 |
| Ammonium Sulphate (65% weight/volume) | 51 | 94 | 341 | 90 | 2.30 | 0 |
| Sodium Sulphate (22% weight/volume) | 50 | 93 | 349 | 92 | 1.54 | 29 |
| Sodium Chloride (10% w/v) | 49 | 91 | 338 | 89 | 0.52 | 76 |

The data in Table 5 demonstrate the successful use of sodium chloride to precipitate alkaline protease similar to other conventional protein-precipitating salts. Moreover, precipitation with sodium chloride achieved superior efficiency in removing pigment in contrast to sodium sulphate and ammonium sulphate.

EXAMPLE 8

Polysaccharide Reduction by Enzymatic Hydrolysis

Alkaline proteases exhibited maximum stability at pH greater than 4.5 in the presence of 10% NaCl at temperatures less than 40° C. Several commercial enzymes which hydrolyse starch and pectins were tested. Pec- Bacillus alcalophilus alkaline protease samples (activity—is 1,000,000 Delft units/ml) add 5 ml H$_2$O, mix and then slowly and carefully add 1 ml of concentrated hydrochloric acid. Centrifuge the mixture (15,000 rpm, 20 min SS-34 rotor) and then decant the supernatant into a screw-cap test tube. Place in an oven at 100° C. for 24 hours. After this time, dilute the hydrolyzate 1:1 with mobile phase, filter through a 0.45µ filter and analyze by high performance liquid chromatography. Known concentrations of galactose and glucose are used to calibrate the detector.

| HPLC Analysis of Galactosyl Polymer Hydrolyzate | |
|---|---|
| Conditions: | |
| Column | HPX-87H (Bio Rad) |
| Mobile Phase | 0.01N H$_2$SO$_4$ |
| Temperature | 60° C. |
| Flow Rate | 0.7 ml/min |
| Sample Volume | 20 μl |
| Detector | Refractive Index |

TABLE 6

Effect of Pectinase/Glucoamylase Treatment on the Reduction of Galactosyl Polymer Content

| Incubation Time, Hours | Percent Redutions |
|---|---|
| 0 | |
| 6 | 94.0 |
| 12 | 95.1 |
| 24 | 96.5 |
| 48 | 96.6 |
| 72 | 97.2 |

Figure 4A:
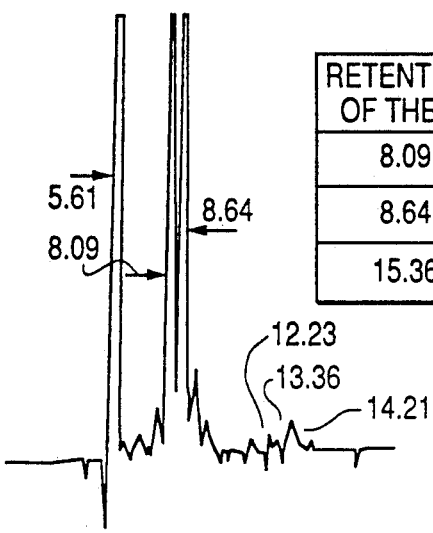
FIG. 4 is the high performance liquid chromatographic patterns of alkaline protease preparations in the unpurified, sodium chloride precipitated, and sodium chloride and hydrolytic enzyme treated samples of alkaline protease derived from *Bacillus alcalophilus*.
Figure 4B:
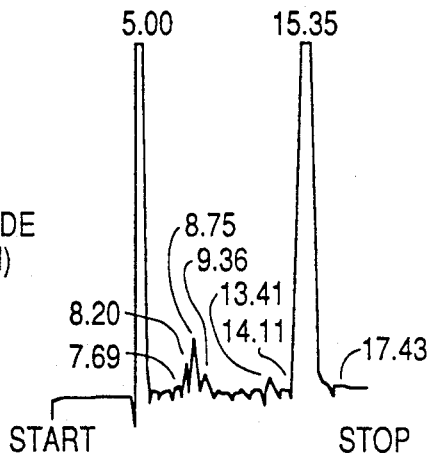
Figure 4C:
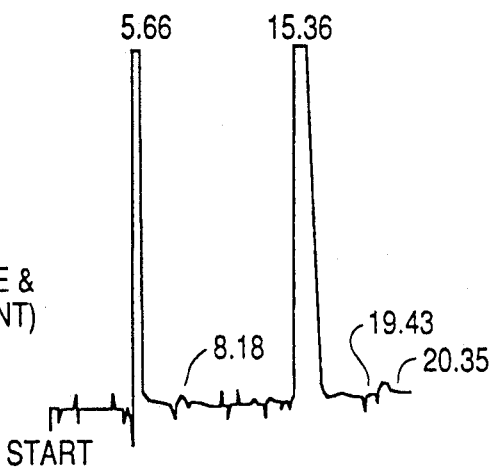

Hydrolytic enzymes treatment of *Bacillus alcalophilus* ultrafiltrate concentrate resulted in a significant reduction of galactose containing polymer. *Bacillus alcalophilus* alkaline protease (Opticlean ®) precipitate of hydrolytic enzyme treated ultrafiltrate concentrate with sodium chloride resulted in Opticlean ® essentially free from galactose polymer (FIG. 4).

It is preferred to collect the alkaline protease precipitate by cross flow membrane filtration where conditions allow. This operation results in a highly purified alkaline protease from *Bacillus alcalophilus* with no detectable levels of galactosyl polymer, and significantly reduced pigment content, e.g., the absorption at 470 nm is less than 1.3. This result is based on an enzyme concentrate with an activity of 1,000,000 Delft units/g.

EXAMPLE 9

Effect Of Various Sodium Halides

To separate one hundred ml aliquots of the alkaline protease ultrafiltration concentrate (403 DAPU/ml, 48.3 g/l), sodium fluoride, sodium chloride, sodium bromide and sodium iodide were added to final concentrations of 0.5M. The pH of the solution was adjusted to 7.5 using 2N NaOH. The alkaline protease solutions containing the different salts were then incubated at 37° C. for four hours. The precipitate was then separated from the supernatant by centrifuging at 16,000 rpm at 5° C., for 20 min and the pellet dissolved in a 50% propylene glycol solution (100 ml). The total protein and enzymatic activity of the pellet were determined (Table 7).

TABLE 7

| | Effect of Sodium Halides | | | |
|---|---|---|---|---|
| | Protein | | Protease Activity | |
| Sodium Halide (0.5 M) | mg/ml | % precipitated | DAPU/ml | % enzyme precipitated |
| — | 59.0 | 0 | 403.0 | 0 |
| Sodium fluoride | 0.8 | 1.4 | 3.0 | 0.7 |
| Sodium chloride | 45.0 | 76.4 | 302.5 | 75.0 |
| Sodium bromide | 8.0 | 14.0 | 54.0 | 13.4 |
| Sodium iodide | 2.3 | 3.9 | 15.6 | 3.9 |

Sodium chloride was found to be the best precipitant among the halides tested. It is also apparent that precipitation of the enzyme could not be attributed to any property generic to halogen atoms. In fact, essentially no precipitation of the enzyme occurred when sodium fluoride and sodium iodide were used. Magnesium chloride and potassium chloride also caused the precipitation of alkaline protease similar to sodium chloride whereas calcium chloride had no effect on alkaline protease precipitation under identical conditions.

EXAMPLE 10

Effect of pH on the Aqueous Stability of Alkaline Protease at 37° C.

Figure 2:
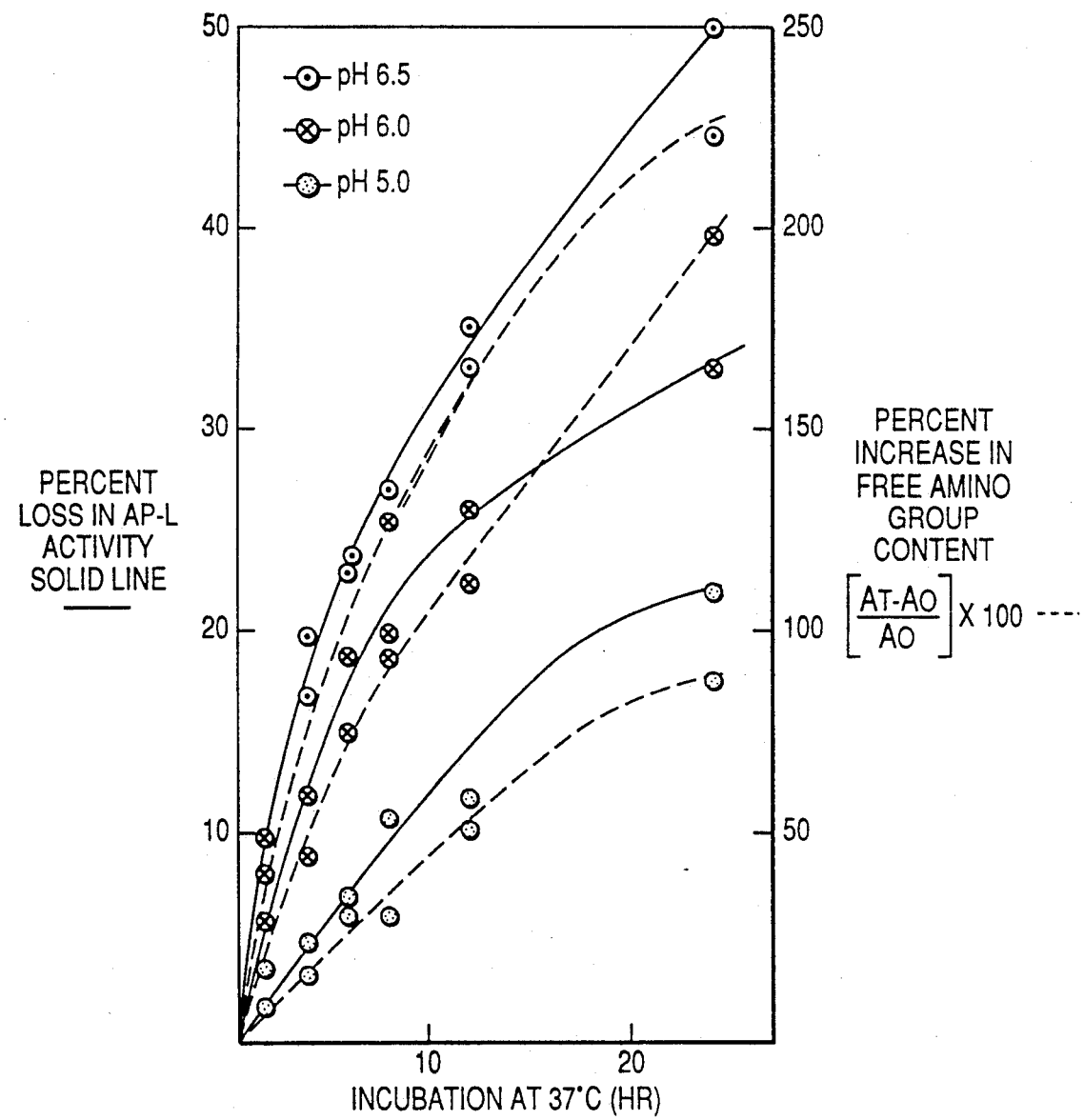
FIG. 2 is a graphical depiction of the effect of pH on the autolytic degradation of alkaline protease from *Bacillus licheniformis* at 37° C.

Alkaline protease concentrate, 100 ml (430 DAPU/ml) was adjusted to pH 6.5, 6.0 and 5.0 using 20% (w/v) acetic acid. The solutions were filtered through 0.45μ filters (cold sterilization). The samples were then maintained at 37° C., and aliquots (10 ml) were withdrawn at different intervals of time and frozen immediately to arrest the reaction. The pH of the solutions was maintained by the addition of 8% sodium hydroxide. The effect of pH on the aqueous stability of the enzyme at 37° C. was determined by measuring the protease activity of the sample. The extent of proteolytic degradation of the enzyme was measured by determining the increase in the amount of free amino groups. The data presented in FIG. 2 show that the aqueous stability of the enzyme decreases with the increasing pH of the solution. The loss of enzymatic activity (solid line) correlates to the increase in the free amino group content (dotted line). The increase in the free amino group content during incubation of alkaline protease strongly suggests proteolytic degradation of the enzyme. Incubation of alkaline protease at pH 6.5 at 37° C. for 24 hours resulted in approximately 50% loss in the enzyme activity whereas pH 5.0 incubation resulted in only 20% loss in the enzyme activity.

Total free amino group content of the protein samples was determined by following the method described in R. Fields, *Methods in Enzymology*, Vol. 25, 465 (1972) using trinitrobenzene sulphonic acid (TNBS). The sample containing amino groups was added to 0.5 ml of borate buffer (1 liter of 0.1M Na$_2$B$_4$O$_7$ in 0.1M NaOH) and the volume was made up to 1.0 ml. Then 0.02 ml of 1.1M TNBS solution was added and the solution rapidly mixed. After 5 minutes, the reaction was stopped by adding 2 ml of 0.1M NaH$_2$PO$_4$ which contained 1.5 mM sulphite, and the absorbance at 420 nm was determined. A blank was also prepared. The amount of the amino groups was determined by reference to a standard graph constructed using glycine.

EXAMPLE 11

Effect of Sodium Chloride on the Precipitation of Alkaline Proteases in the Alkaline pHs The precipitation of alkaline proteases by sodium chloride in the alkaline pH regions was tested (pH<7.0). To one liter each of ultrafiltration concentrate of *Bacillus licheniformis* alkaline protease (Optimase ®) (1037 DAPU/g) and *Bacillus alcalophilus* alkaline protease (Opticlean ®) (1,102,000 Delft units/g), pectinase and glucoamylase were added. The pH of the solutions was adjusted to 5.0 using 10% acetic acid and incubated at 30° C. for 6 hours. During incubation, the solutions were constantly stirred. After the specified time, 100 g each of the sample was adjusted to different pHs i.e., 5.5, 6.5, 7.5, 8.5, and 9.5 with 10% sodium hydroxide and solid sodium chloride was added to a final concentration of 10% weight/volume. The mixture was then incubated at 30° C. for 48 hours with constant stirring. The precipitated enzyme was separated by centrifugation. The precipitate was then dissolved in propylene glycol (100 g of 60% propylene glycol) and the enzyme activity was determined. (Table 8)

TABLE 8

Effect of Sodium Chloride on the Precipitation of Alkaline Proteases in the Alkaline pH

| pH of the Precipitation | PERCENT PRECIPITATION | |
|---|---|---|
| | B. licheniformis (Optimase ®) | B. alcalophilus (Opticlean ®) |
| 5.5 | 98 | 91 |
| 6.5 | 95 | 67 |
| 7.5 | 95 | 14 |
| 8.5 | 100 | 4 |
| 9.5 | 95 | 0 |

Incubation of alkaline protease ultrafiltrate concentrate with hydrolytic enzymes at pH 5.0; 30° C. for 6 hours in the absence of sodium chloride resulted in approximately 20-25 loss of the enzymatic activity (autolytic degradation). The results in Table 8 showed that alkaline protease from *Bacillus licheniformis* (Optimase ®) was precipitated by the sodium chloride in the alkaline pH region pH 7.5-9.5 whereas in the case of *Bacillus alcalophilus* (Opticlean ®) the separation of the enzymes occurred only in the acidic pH. The marked difference in the precipitation behavior between the two alkaline proteases by sodium chloride further demonstrates that alkaline protease from different species of Bacilli are probably not functionally or structurally equivalent.

EXAMPLE 12

Effect of Sodium Chloride on the Acid Stability of *Bacillus licheniformis* and *Bacillus alcalophilus*

To ninety grams each of ultrafiltrate concentrate of *Bacillus licheniformis* alkaline protease and *Bacillus alcalophilus* alkaline protease (Optimase ®—1037 DAPU/g and Opticlean ®—1,217,500 Delft units/g), sodium chloride was added to a concentration of 10% and the pH adjusted to 4.0, 4.5, 5.0 and pH 5.5. Clarex ® L pectinase (1.0% volume/volume) and Diazyme ® L-200 glucoamylase (0.25% volume/volume) were added (1.0% volume/volume) and incubated for 48 hrs at 30° C. After the specified time, the precipitated alkaline protease was separated by centrifugation at 15,000 rpm for 45 min., 5° C. The precipitate was then solubilized in 60% propylene glycol (pH 5.2). The enzyme activity was measured. (Table 9)

TABLE 9

Effect of Sodium Chloride on the stability of alkaline protease derived from *Bacillus licheniformis* and *Bacillus alcalophilus* during precipitation in the acidic pH

| | *Bacillus licheniformis* Alkaline Protease | | *Bacillus alcalophilus* Alkaline Protease | |
|---|---|---|---|---|
| pH | DAPU/g | % Precipitation | Delft units/g | % Precipitation |
| 4.0 | 821 | 88 | 1,071,000 | 97.7 |
| 4.5 | 858 | 92 | 1,072,000 | 97.8 |
| 5.0 | 878 | 94 | 1,085,000 | 99.0 |
| 5.5 | 794 | 85 | 915,000 | 84.0 |

As can be seen from the above table, precipitation behavior with the two different enzymes was different at varying pH level. Specifically, *Bacillus licheniformis* alkaline protease showed maximum precipitation in the pH range between pHs 4.5-5.0 whereas *Bacillus alcalophilus* showed maximum precipitation in the wider range of pH of 4.0 to 5.0.

Comparison of these results indicates enhancement of alkaline protease stability by the addition of sodium chloride at acidic pH ranges and at higher temperatures.

EXAMPLE 13

Effect of temperature on the solubility of *Bacillus alcalophilus* alkaline protease in presence of 10% Sodium Chloride To 500 g of *Bacillus alcalophilus* alkaline protease (Opticlean ®) ultrafiltrate concentrate at 5° C., solid sodium chloride was added to a final concentration of 10% weight/volume. The pH was adjusted to pH 5.5. Samples were then incubated at 5° C., 24° C. (room temperature), 30° C., 35° C. and 40° C. for 30 hrs. After this time samples (20 g) were withdrawn and centrifuged at 15,000 rpm. The effect of temperature on enzyme precipitation was determined by measuring the enzymatic activity of the supernatant. To the remaining 80 g of the incubated samples, 80 g of propylene glycol was added and stirred for 16 hrs. at room temperature. The stability of the alkaline protease was then determined by measuring the enzymatic activity. The effect of temperature on the solubility and stability of *Bacillus alcalophilus* alkaline protease is given in Table 10.

TABLE 10

Effect of Temperature on the Solubility and Stability of *Bacillus alcalophilus* Alkaline Protease

| Temperature ° C. | Stability | | *Bacillus alcalophilus* Alkaline Protease Initial Activity | | |
|---|---|---|---|---|---|
| | Delft unit/g | % Loss | Delft unit/g | Supernatant % | Precipitated |
| 5 | 489,000 | 0 | 1,030,800 | 1,030,800 | 0 |
| 24 | 465,200 | 4.3 | | 184,600 | 82.1 |
| 30 | 472,300 | 3.5 | | 112,500 | 89.1 |
| 35 | 467,700 | 4.4 | | 62,000 | 94.0 |
| 40 | 489,000 | 0.1 | | 78,900 | 92.4 |

The data in the above table showed that *Bacillus alcalophilus* alkaline protease is stable at pH 5.5 in the presence of 10% NaCl even at 40° C. for 30 hrs. It is also interesting to note that the separation of the enzyme increased with increasing temperature. More than 90% of the enzyme was precipitated above 30° C.

EXAMPLE 14

Cross Flow Membrane Filtration (Microfiltration) of Bacillus alcalophilus Alkaline Protease Precipitates Cross flow membrane filtration commonly referred as microfiltration is becoming an increasingly common technique to separate the insoluble solids. Contained operation of cross flow systems is generally regarded to be less problematical compared with centrifugation. Cross flow filtration is essentially a non-cake forming method. It has been suggested that cross flow filtration can be more economical than a moderately slow rotary vacuum filtration and/or filter press (Beaton, N.C. 1980. Appl. of Ultrafiltration to Ferment. Prod., Polymer Science Technol. Plenum, N.Y. 13.) High permeate flow rates, 67–118 liter/m$^2$/hr are possible during the concentration of bacterial suspensions (Henry, J. D., *Cross Flow Filtration, Recent Dvpts.*, Sep. Science. Li, N.M. (ed)., CRC Press 2, 205 (1972)). Rotary drum filtration or filter press filtration is not a preferred method to separate insolubles during processing of alkaline proteases because of the generation of aerosols containing enzymes which may cause allergic reactions. Since microfiltration can be a unit operation, the inherent problems of dead-end filtration methods do not exist. Thus, microfiltration offers additional environmental safety when processing alkaline proteases in a large scale operations.

Addition of filter aid (diatomaceous earth) is needed during the dead-end filtration which latter becomes as a solid waste. Microfiltration is a gentle technique and does not require chemical additives or filter aids. To two hundred liter of *Bacillus alcalophilus* alkaline protease ultrafiltrate concentrate (1,086,000 Delft units/g), sodium chloride was added to a final concentration of 10% (weight/volume). Glucoamylase (Clarex ® 1.0% volume/volume) and pectinase (Diazyme ® L-200 0.25% volume/volume) were added. The pH was adjusted to pH 5.2 and incubated at 30° C. for 48 hours. The precipitated enzyme was separated from the mother liquor using microfiltration (Koch #603, —4" cartridge, 0.1μ pore/size; Koch Membrane Systems, Inc., 850 Main Street, Wilmington, Mass. 01887-3388, USA). The concentrated slurry was then diafiltered twice with 10% sodium chloride solution to remove pigment and other soluble impurities. After the diafiltration, the enzyme was solubilized in propylene glycol by circulating 70% propylene glycol containing 10% calcium chloride. The process resulted in over 80% recovery of the alkaline protease with low color (98% reduction) and essentially free from galactosyl polymer (FIG. 4).

EXAMPLE 15

The purified alkaline protease concentrate of Example 14 was granulated. The process used is that described in U.S. Pat. No. 4,689,297 to Good et al. entitled "Dust free Particulate Enzyme Formulation" (Aug. 25, 1987), which is incorporated by reference.

In a typical experiment, following composition was used:

| Purified *Bacillus alcalophilus* Alkaline Protease Concentrate 43.6% DS, 5.5 × 10$^6$ DU/g. 100% DSB Enzyme Formulation | | |
|---|---|---|
| Materials | % Dry Solid Base | Procedure |
| Enzyme | 67.1 | The enzyme solution was diluted |
| Precipitate (5,500,000 DU/g) | | to 26% DS and spray coated onto 1000 g NaCl in a Uni Glatt |
| Iconol | 15.4 | using a Wurster insert. |
| Polyvinyl Alcohol | 7.7 | |
| Atgel | 9.8 | |
| Cosmetic Formulation | | |
| TiO$_2$ | 60 | Cosmetic slurry was diluted to |
| Talc | 15 | 30% DS and spray coated onto |
| Polyvinyl Alcohol | 11 | enzyme coated NaCl in a Uni Glatt using a Wurster insert. |
| Iconol | 14 | After coating with 17% w/w/ (final product basic) of cosmetic solids the granules were sieved -20 + 60. |

This formulation resulted in an acceptable spray-coated product having desirable properties for use in granular detergent formulations, and other suitable uses.

EXAMPLE 16

The purified precipitate concentrate of Example 14 was used to make marums according to the following formula, and in accordance with the stated procedure:

| Purified *Bacillus alcalophilus* Alkaline Protease Concentrate 49.6% Dry Solid. 3.1 × 10$^6$ Delft Units/g. 81.7% Dry Solid Base enzyme crystals/19% Dry Solid Base FW2 Marums Formulations | | |
|---|---|---|
| Materials | % Dry Solid Base | Procedure |
| Bentonite | 27.6 | All non-soluble |
| BW-300 | 24.7 | materials were dry |
| Polyethylene glycol (PEG-3350) | 15.3 | mixed. Soluble materials were mixed into a |
| Kaolin | 5.2 | slurry. The slurry and |
| Na$_2$SO$_4$ | 1.8 | non-soluble materials |
| Polyethylene glycol (PEG-8000) | 0.9 | were blended together at a moisture content of |
| Propylene Glycol | 0.9 | 23% water. The mixture |
| Enzyme Crystals | 19.1 | was extruded a 0.7 mm |
| Diatomaceous earth (FW2) | 4.5 | die, dried in a Uni Glatt fluid bed dryer. |
| Added H$_2$O | 5 | |

EXAMPLE 17

Effect of pH on Precipitation of *Bacillus licheniformis* Alkaline Protease

As shown in Table 11, excellent yield percentages were obtained in the pH range of from 4.0 to 4.5. These values are a significant improvement over the precipitation yield in the 5.3 to 5.5 pH range.

TABLE 11

| Effect of PH on Precipitation of Alkaline Protease Derived From *Bacillus licheniformis* | | |
|---|---|---|
| Trial | pH of the Precipitation | % Enzyme Precipitated |
| 1 | 5.3–5.5 | 87.8 |
| 2 | 5.3–5.5 | 89.6 |
| 3 | 5.3–5.5 | 86.9 |
| 4 | 5.3–5.5 | 88.0 |
| | | AV = 88.08 |
| 5 | 4.5 | 97.9 |
| 6 | 4.5 | 95.3 |
| 7 | 4.0 | 98.5 |

TABLE 11-continued

Effect of PH on Precipitation of Alkaline
Protease Derived From *Bacillus licheniformis*

| Trial | pH of the Precipitation | % Enzyme Precipitated |
|---|---|---|
| | | AV = 97.2 |

Of course, it should be understood that a wide range of changes and modifications can be made to the preferred embodiment described above. It is therefore intended that the foregoing detailed description be understood that it is the following claims, including all equivalents, which are intended to define the scope of this invention.

We claim:

1. A method for the isolation of highly purified alkaline protease from a fermentation broth, wherein said alkaline protease is derived from either *Bacillus licheniformis* or *Bacillus alcalophilus*, comprising:
   (i) forming an alkaline protease solution by separating the alkaline protease from cells and suspended solids in said fermentation broth;
   (ii) concentrating said alkaline protease solution;
   (iii) adding to said concentrated alkaline protease solution hydrolytic enzymes capable of hydrolyzing starch and pectins and sodium chloride in an amount effective to precipitate said alkaline protease;
   (iv) incubating the mixture to separate said alkaline protease from hydrolyzed polymeric impurities and dissociate said alkaline protease from pigments, at a temperature of at least 20° C. and for a time effective to precipitate said alkaline protease; and
   (v) collecting a purified alkaline protease precipitate; wherein said alkaline protease defines a galactosyl polymer content of less than 1.00 mg/g of enzyme protein.

2. The method according to claim 1, wherein steps (iii) through (v) are carried out under conditions which include agitation.

3. The method according to claim 1, wherein said alkaline protease is derived from *Bacillus licheniformis* and steps (iii) through (v) are carried out at a pH of between about 4.5 and 9.5.

4. The method according to claim 1, wherein said alkaline protease is derived from *Bacillus alcalophilus* and steps (iii) through (v) are carried out at a pH of between about 4.0 and 7.5.

5. The method according to claim 1, wherein steps (iii) through (v) are carried out at a temperature between about 28° C. and 32° C.

6. The method according to claim 1, wherein said concentrated alkaline protease solution is at a pH of between about 3.5 and 5.5 during the addition of said hydrolytic enzymes and raised to a pH of between about 6.0 and 9.0 with the addition of sodium chloride.

7. A method for the isolation of highly purified alkaline protease from a fermentation broth, wherein said alkaline protease is derived from *Bacillus alcalophilus*, comprising:
   (i) forming an alkaline protease solution by separating the alkaline protease from cells and suspended solids in said fermentation broth;
   (ii) concentrating said alkaline protease solution;
   (iii) adding to said concentrated alkaline protease solution hydrolytic enzymes capable of hydrolyzing starch and pectins and sodium chloride in an amount effective to precipitate said alkaline protease;
   (iv) incubating the resultant mixture to separate said alkaline protease solution from hydrolyzed polymeric impurities and dissociate said alkaline protease from pigments at a temperature of at least 20° C. and for a time effective to precipitate said alkaline protease; and
   (v) collecting a pure alkaline protease precipitate being essentially amorphous and presenting a crystalline structure content of less than 20%; wherein said alkaline protease defines a galactosyl polymer content of less than 1.00 mg/g of enzyme protein.

8. A method for the isolation of purified alkaline protease from a fermentation broth, wherein said alkaline protease is derived from *Bacillus licheniformis*, comprising;
   (i) forming an alkaline protease solution by separating the alkaline protease from cells and suspended solids in said fermentation broth;
   (ii) concentrating said alkaline protease solution;
   (iii) adding to said concentrated alkaline protease solution hydrolytic enzymes capable of hydrolyzing starch and pectins and sodium chloride in an amount effective to precipitate said alkaline protease;
   (iv) incubating the resultant mixture to separate said alkaline protease solution from hydrolyzed polymeric impurities and dissociate said alkaline protease from pigments at a temperature of at least 20° C. and for a time effective to precipitate said alkaline protease; and
   (v) collecting a pure alkaline protease precipitate being essentially amorphous and presenting a crystalline structure content of less than 40%; wherein said alkaline protease defines a galactosyl polymer content of less than 1.00 mg/g of enzyme protein.

* * * * *